US010816546B2

(12) United States Patent
Kilaas et al.

(10) Patent No.: US 10,816,546 B2
(45) Date of Patent: Oct. 27, 2020

(54) BINDING A TARGET SUBSTANCE

(71) Applicant: SINVENT AS, Trondheim (NO)

(72) Inventors: Lars Kilaas, Trondheim (NO); Anne Dalager Dyrli, Trondheim (NO); Vidar Skagestad, Haslum (NO)

(73) Assignee: Sinvent AS, Trondheim (NO)

( * ) Notice: Subject to any disclaimer, the term of this patent is extended or adjusted under 35 U.S.C. 154(b) by 1179 days.

(21) Appl. No.: 14/810,216

(22) Filed: Jul. 27, 2015

(65) Prior Publication Data

US 2015/0329851 A1 Nov. 19, 2015

Related U.S. Application Data

(62) Division of application No. 10/519,167, filed as application No. PCT/IB03/02994 on Jul. 1, 2003, now abandoned.

(30) Foreign Application Priority Data

Jul. 1, 2002 (GB) .................................. 0215185.0

(51) Int. Cl.
*H01F 1/11* (2006.01)
*G01N 33/543* (2006.01)
*C12N 15/10* (2006.01)

(52) U.S. Cl.
CPC ... *G01N 33/54393* (2013.01); *C12N 15/1013* (2013.01); *G01N 33/54326* (2013.01); *G01N 33/54333* (2013.01); *H01F 1/11* (2013.01); *Y10T 428/2982* (2015.01)

(58) Field of Classification Search
CPC ....... G01N 33/54326; G01N 33/54393; C12N 15/1013; H01F 1/11
See application file for complete search history.

(56) References Cited

U.S. PATENT DOCUMENTS

| 4,157,323 | A | | 6/1979 | Yen et al. |
|---|---|---|---|---|
| 4,329,241 | A | | 5/1982 | Massart |
| 4,343,901 | A | | 8/1982 | DeFilippi |
| 4,452,773 | A | | 6/1984 | Molday |
| 4,454,234 | A | | 6/1984 | Czerlinski |
| 4,554,088 | A | * | 11/1985 | Whitehead ......... B01D 15/1807 252/62.51 R |
| 4,620,987 | A | | 11/1986 | Yamashita et al. |
| 4,661,408 | A | | 4/1987 | Lau et al. |
| 4,863,715 | A | | 11/1989 | Jacobsen et al. |
| 5,091,206 | A | | 2/1992 | Wang et al. |
| 5,320,944 | A | | 6/1994 | Okada et al. |
| 5,395,498 | A | | 3/1995 | Gombinsky et al. |
| 5,395,688 | A | | 3/1995 | Wang et al. |
| 5,445,970 | A | | 8/1995 | Rohr |
| 5,523,231 | A | | 6/1996 | Reeve |
| 5,597,531 | A | | 1/1997 | Liberti et al. |
| 5,601,979 | A | | 2/1997 | Wong |
| 5,648,124 | A | | 7/1997 | Sutor |
| 5,705,628 | A | | 1/1998 | Hawkins |
| 5,876,593 | A | * | 3/1999 | Liberti .................... B03C 1/002 210/222 |
| 5,945,525 | A | | 8/1999 | Uematsu et al. |
| 5,962,641 | A | | 10/1999 | Nelson et al. |
| 5,990,302 | A | | 11/1999 | Kuroita et al. |
| 6,027,945 | A | | 2/2000 | Smith et al. |
| 6,027,946 | A | | 2/2000 | Weitschies et al. |
| 6,255,477 | B1 | | 7/2001 | Kleiber et al. |
| 6,264,814 | B1 | | 7/2001 | Lange |
| 6,284,470 | B1 | * | 9/2001 | Bitner ..................... C12N 1/02 435/6.16 |
| 6,355,792 | B1 | | 3/2002 | Michelsen et al. |
| 6,548,264 | B1 | | 4/2003 | Tan et al. |
| 2001/0007713 | A1 | | 7/2001 | Pryor et al. |
| 2002/0000398 | A1 | | 1/2002 | Skold |
| 2007/0225488 | A1 | * | 9/2007 | Skold ....................... B03C 1/01 536/55.3 |

FOREIGN PATENT DOCUMENTS

| EP | 0 125 995 | A2 | 11/1984 |
|---|---|---|---|
| EP | 0 757 106 | A2 | 2/1997 |
| EP | 1 069 131 | A1 | 1/2001 |
| EP | 1 376 129 | A2 | 1/2004 |
| JP | 8-259607 | A | 10/1996 |
| JP | 2000-306718 | A | 11/2000 |
| WO | 88/06632 | A1 | 9/1988 |
| WO | 96/18731 | A2 | 6/1996 |
| WO | 97/22366 | A1 | 6/1997 |
| WO | 99/01900 | A1 | 1/1999 |
| WO | 99/19000 | A1 | 4/1999 |
| WO | 01/37291 | A1 | 5/2001 |
| WO | 01/71732 | A2 | 9/2001 |

(Continued)

OTHER PUBLICATIONS

Dynabeads et al. (Dynabeads protocol Cat. No. 370.02D, Invitrogen Dynal AS, Oslo, Norway) (Year: 2008).*
Atkins et al., "Colloids" in *Physical Chemistry 7th Edition*, Oxford University Press, New York City, 2002, pp. 752-754.
Chantrell et al., "The isothermal remanent magnetisation of fine magnetic particles," Journal of Physics D: Applied Physics, 18:2505-2517, 1985.
Cullity, Introduction to Magnetic Materials, Addison-Wesley Publishing Company, Philippines, 1972, pp. 410-425.
Cullity, Introduction to Magnetic Materials, Addison-Wesley Publishing Company, Philippines, 1972, pp. 383-391.

(Continued)

Primary Examiner — Gailene Gabel

(74) Attorney, Agent, or Firm — Seed IP Law Group LLP

(57) ABSTRACT

Magnetic particles capable of binding a target substance, which comprise a magnetic material and a matrix material, wherein the magnetic material is remanent upon exposure to a magnetic field and the matrix material has a surface comprising functional groups which promote disaggregation of the particles in the presence of a liquid phase.

16 Claims, No Drawings

(56) References Cited

FOREIGN PATENT DOCUMENTS

| WO | 01/88540 A1 | 11/2001 |
|---|---|---|
| WO | 02/44414 A2 | 6/2002 |
| WO | 02/075309 A1 | 9/2002 |
| WO | 03/004150 A1 | 1/2003 |
| WO | 03/004151 A1 | 1/2003 |
| WO | 03/095646 A1 | 11/2003 |

OTHER PUBLICATIONS

Ferromagnetism, URL=http://hyperphysics.phy-astr.gsu.edu/hbase/solids/ferro.html, download date Dec. 13, 2010.

Kemshead et al., "Magnetic microspheres and monoclonal antibodies for the depletion of neuroblastoma cells from bone marrow: Experiences, improvements and observations," *Br. J. Cancer* 54: 771-778, 1986.

Lea et al., "Magnetic Monosized Polymer Particles for Fast and Specific Fractionation of Human Mononuclear Cells," Scand. J. Immunol 22: 207-216, 1985.

Meito Sangyo Co., Ltd., Fine Chemicals Division, URL=http://www5.mediagalaxy.co.jp/meito/kaseihin/index_e.html, download date Dec. 13, 2010.

Popescu et al., "The Application of Perturbational Statistical Theories to the Investigation of the Static Magnetization of Magnetic Fluids," *Journal of Optoelectronics and Advanced Materials* 7(2):753-757, Apr. 2005.

Sato et al., Magnetic Properties of Ultrafine Ferrite Particles, Journal of Magnetism and Magnetic Materials 65:252-256, 1987.

Schwertmann et al., Iron Oxides in the Laboratory: Preparation and Characterization, VCH, Weinheim, 1991, pp. 110-132.

Taketomi et al., "Experimental and Theoretical Investigations on Agglomeration of Magnetic Colloidal Particles in Magnetic Fluids," *Journal of the Physical Society* 60(5):1689-1707, May 1991.

Tong et al., "A Novel Magnetic Affinity Support for Protein Adsorption and Purification," Biotechnol. Prog. 17: 134-139, 2001.

Treleaven et al., "Removal of Neuroblastoma Cells From Bone Marrow With Monoclonal Antibodies Conjugated to Magnetic Microspheres," *The Lancet* 323(8368): 70-73, Jan. 14, 1984.

Jiles, *Introduction to Magnetism and Magnetic Materials*, $2^{nd}$ ed., Chapman & Hall, London, United Kingdom, 1998, p. 94-95. (3 pages).

Lapopin et al., "MagNA Pure LC: Evaluation as a Sample Preparation System for the Light Cycler Instrument," *Biochemica* 1:10-16, 2000.

Loeffler et al., "Automated Extraction of Genomic DNA from Medically Important Yeast Species and Filamentous Fungi by Using the MagNA Pure LC System," *Journal of Clinical Microbiology* 40(6):2240-2243, 2002.

Magnusson, "Hydrophobic interaction—a mechanism of bacterial binding," *Scandinavian Journal of Infectious Diseases* 14(Supplement 33):32-36, 1982. (Abstract only).

Mallik et al., "Large positive magnetoresistance at low temperatures in a ferromagnetic natural multilayer, $LaMn_2Ge_2$," *Applied Physics Letters* 71(16):2385-2387, 1997. (4 pages).

Merck, BioBeads: Product Data Sheet, sent by facsimile Apr. 25, 1997, 1 page.

Merck, "Nucleic Acid Separation and Purification," URL=http://www.merck.de/english/services/labor/l_bio/beads.html, download date May 11, 2001, 1 page.

Qiagen, *Ni-NTA Magnetic Agarose Beads Handbook*, $2^{nd}$ ed., 2001, 88 pages.

Richter et al., "Determinants for Removal and Degradation of Transit Peptides of Chloroplast Precursor Proteins," *The Journal of Biological Chemistry* 277(46):43888-43894, 2002. (8 pages).

Sanghi, "What's up with chelates," *Current Science* 78(11):1-5, 2000.

Shen et al., "Points of Zero Charge and Intrinsic Equilibrium Constants of Silica-Magnetite Composite Oxides," *Journal of Colloid and Interface Science* 214(2):333-343, 1999.

Taylor et al., "Application of magnetite and silica-magnetite composites to the isolation of genomic DNA," *Journal of Chromatography A* 890(1):159-166, 2000.

Thompson et al., *Environmental Magnetism*, Allen & Unwin, London, United Kingdom, 1986, p. 3-20. (22 pages).

Williams et al., "Automated DNA Extraction for Real-Time PCR," *Clinical Chemistry* 48(9):1629-1630, 2002.

Myers, D. *Surfaces, Interfaces and Colloids: Principles and Applications*, $2^{nd}$ Edition, 1999, Chapters 4, 5 and 10.

Behrens et al., "The Charge of Glass and Silica Surfaces," *Chem. Phys.*, 115:6716-6721, 2001. (7 pages).

Krupyanskii et al., "Magnetic properties of ultrafine iron oxide particles," *Sov. Phys.-JETP*, 38(4):859-864, 1974.

Nagata et al., "Effect of Nitrogen Uptake on the Curie Temperature of Intermetallic Compounds $R_2Fe_{17}$ and $R_2Fe_{17}C_{0.5}$," *Japanese J. Appl. Phys.*, 30(part 2, No. 3A)—Abstract. (1 page).

Faulmann et al., "Protein B: A Versatile Bacterial Fc-Binding Protein Selective for Human IgA," *BioTechniques* 10(6):748-750, 752-755, 1991 (8 pages).

Hermanson et al., "Immobilized Affinity Ligand Techniques," *Academic Press*, 1992 (18 pages).

\* cited by examiner

BINDING A TARGET SUBSTANCE

FIELD OF THE INVENTION

The present invention relates to magnetic particles capable of binding a target substance such as nucleic acid, a process for making such magnetic particles, and a process for isolating a target substance from a target substance-containing sample.

BACKGROUND TO THE INVENTION

Procedures involving nucleic acids such as DNA and RNA continue to play a crucial role in biotechnology. Nucleic acid detection and manipulation including hybridisation, amplification, sequencing and other processes generally require nucleic acid to have been isolated from contaminating material. Where a nucleic acid-containing sample is a biological sample, contaminating material may include proteins, carbohydrates, lipids and polyphenols. Accordingly, a variety of approaches have hitherto been used in the isolation of DNA or RNA.

Early methods of isolating nucleic acid involved a series of extractions with organic solvents, involving ethanol precipitation and dialysis of the nucleic acids. These early methods are relatively laborious and time-consuming and may result in low yield. Isopropanol may also be used in the precipitation of the nucleic acid.

An alcohol precipitation method is described in U.S. Pat. No. 5,523,231. Nucleic acid is precipitated by highly concentrated alcohol in the presence of magnetic beads. The precipitate can be separated from supernatant by the application of a magnetic field.

U.S. Pat. No. 5,395,498 describes a method for isolating biological macromolecules from electrophoretograms using a matrix of magnetic particles which have an affinity to the molecules separated on the electrophoretogram. Magnetic particles are described with a range of various magnetic substances, those having essentially no magnetic memory being preferred. A magnetic field is used to attract the magnetic particles to a specific location in the electrophoretogram for specific binding of the particles to a specific species of biological macromolecule, typically separated as a band in the electrophoretogram.

U.S. Pat. No. 6,027,945 describes a method which uses a silica-based nucleic acid binding solid phase in the presence of a chaotrope to isolate nucleic acid. According to this method, the silica-based solid phase is magnetic, thereby facilitating separation of the solid phase containing the target nucleic acid from the liquid phase containing contaminants upon application of a magnetic field. A similar method is described in U.S. Pat. No. 5,945,525.

U.S. Pat. No. 5,990,302 describes a method for isolating RNA which is also performed in the presence of a chaotrope. A sample is mixed with an acidic solution containing a lithium salt, a chaotropic agent and a nucleic acid-binding carrier to absorb the RNA onto the carrier. The RNA-bound carrier is isolated from the liquid phase and eluted. Magnetic silica particles are used as the nucleic acid-binding carrier, although silica, cellulose, nitrocellulose, latex and hydroxyapatite are all mentioned as possible carriers.

WO96/18731 also uses magnetic particles to bind nucleic acid. In this disclosure the magnetic particles are polystyrene-based and polyurethane-coated and a detergent is used instead of a chaotrope.

U.S. Pat. No. 5,705,628 discloses a method of separating polynucleotides, especially DNA, by binding the polynucleotides to a magnetic micro particle having a functional group-coated surface.

All of the prior art documents described herein and each of their commercial counterparts known to the present applicants use magnetic particles which are capable of being magnetised in the presence of a magnetic field but which are not themselves magnetic in the absence of such a field. Paramagnetic or superparamagnetic materials possess these qualities. It has hitherto been thought that particles which are themselves magnetic in the absence of a magnetic field (and which are known as remanent particles) are undesirable because they disadvantageously form aggregates because of their remanence. These aggregates prevent intimate mixture with sample and are therefore considered to inhibit partially binding of nucleic acid from the sample to the magnetic particles.

Contrary to this generally-held thinking, the present applicants have surprisingly found that remanent magnetic particles may be advantageously used in isolating nucleic acid and other target substances.

SUMMARY OF THE INVENTION

Accordingly, in a first aspect, the present invention provides magnetic particles capable of binding a target substance, which comprise a magnetic material and a matrix material, wherein the magnetic material is remanent upon exposure to a magnetic field and the matrix material has a surface comprising functional groups which promote disaggregation of the particles in the presence of a liquid phase.

It has surprisingly been found that remanent magnetic particles can be extremely effective in separation or isolation of target substances from a sample. Remanent magnetic particles according to the present invention may form aggregates when suspended in a liquid phase but are readily dispersible upon application of a force to disrupt the aggregates. Advantageously, the matrix material of the magnetic particles has a surface comprising functional groups which promote this disaggregation of the particles in the presence of the liquid phase.

Because the magnetic particles are remanent, they are highly responsive to magnetic fields. The particles can be made smaller than conventional magnetic particles and yet respond quickly to a magnetic field. This has an advantage that the smaller the particle, generally the higher the binding capacity. Accordingly, the invention allows the use of high capacity, small particles which are still capable of obtaining a fast separation, as compared with larger conventional particles. Particles according to the invention are superior to paramagnetic and superparamagnetic particles of the same size in terms of velocity in a magnetic field. This is an enormous advantage regarding isolation. In automatic systems it becomes possible to increase the number of samples to be analysed dramatically.

The magnetic material which forms part of the magnetic particles is remanent in the sense that, upon exposure to a magnetic field, the material must have residual magnetisation in the absence of a magnetic field. Accordingly, in the present specification remanence encompasses both materials which have been previously exposed to a magnetic field and therefore have residual magnetisation and those materials which currently have no residual magnetisation but will develop this feature following exposure to the magnetic field. These properties of magnetic materials according to the present invention contrast those in the prior art such as U.S. Pat. Nos. 6,027,945 or 5,945,525 in which the magnetic particles are paramagnetic or superparamagnetic and are not themselves magnetic in the absence of a magnetic field.

The magnetic material according to the present invention advantageously comprises a ferrimagnetic material. Whilst some texts define a ferrimagnetic material as one which contains iron, according to the present specification, a ferrimagnetic material is one which may be a metal or a metal oxide and may or may not contain iron. In one embodiment, the ferrimagnetic material comprises a ferrimagnetic metal oxide which preferably comprises an iron oxide. Optionally all or a part of the ferrous iron of the metal or metal oxide may be substituted by a divalent transition metal selected from cadmium, chromium, cobalt, copper, magnesium, manganese, nickel, vanadium, and/or zinc. A particularly preferred ferrimagnetic metal oxide comprises ferrimagnetic magnetite.

In another embodiment of the present invention, the magnetic material is ferromagnetic, and preferably contains iron. The ferromagnetic material may be metal or metal oxide. Optionally, all or part of the iron of the metal or metal oxide may be substituted with another divalent transition metal as above.

The length or diameter of the magnetic particles is typically in the range 0.1 to 5,000 µm, preferably in the range 0.1 to 1,000 µm, more preferably in the range 0.1 to 500 µm, most preferably in the range 0.1 to 100 µm. It is found that smaller particles can be separated quickly in a magnetic field and will have high binding capacity. It is preferred that the magnetic particles are substantially spherical because particles of this shape disaggregate more easily.

The matrix material of the magnetic particles may comprise any material suitable to facilitate binding of the target substance. The composition of the matrix material will therefore depend to some extent on the nature of the target substance to be bound by the magnetic particles. The matrix material may provide a coating or shell for the magnetic material and may bind or complex with the magnetic material or form a composite therewith. In one arrangement the matrix material comprises a polymer which may be an organic polymer or an inorganic polymer such as a silica-based polymer. Where the matrix material is inorganic, this may alternatively comprise salts or molecules.

It is advantageous for the surface of the magnetic particles to comprise functional groups which promote disaggregation of the magnetic particles in the presence of a liquid phase. These functional groups may arise because of the nature of the matrix material used in the magnetic particles. Alternatively, the matrix material may need to be treated in order to introduce those functional groups. In one arrangement, the functional groups of the matrix material are hydrophilic for use with an aqueous liquid phase. For example, where the aqueous liquid phase arises from a biological sample, a matrix material having a hydrophilic surface would be easier to disaggregate than a matrix material having a hydrophobic surface. In the alternative, magnetic particles may be provided in which the functional groups of the matrix material are hydrophobic for use with an organic liquid phase, especially a non-polar liquid phase. Where a non-polar liquid phase is used, a hydrophilic surface on the magnetic particles would make the particles more difficult to disaggregate. It is also possible for the surface to have a combination of both hydrophilic and hydrophobic groups. Such a combination is preferred where solvent systems miscible with both water and non-poplar solvents are used, such as THF, DIGLYMR and DMSO.

The functional groups may also affect the binding properties of the particles in relation to the target substance. The capability of the magnetic particles to bind the target substance may be conferred by the bulk properties of the matrix material or by the matrix material further comprising an affinant for binding the target substance. Affinant chemistry and methodology is discussed in further detail in "Immobilised Affinity Ligand Techniques" by Hermanson et at (1992). The surface properties and affinant properties of the magnetic particles will be discussed in further detail below in relation to various different target substances.

In a further aspect the present invention provides a process for the preparation of magnetic particles capable of binding a target substance, which comprises providing an unmagnetised magnetic material, and providing a matrix material so as to form magnetic particles, wherein the magnetic material is remanent upon exposure to a magnetic field and the matrix material has a surface comprising functional groups which promote disaggregation of the particles in the presence of a liquid phase.

The matrix material may comprise a polymer which, as discussed above, may be inorganic or organic. The process may be performed in a number of ways. According to one embodiment, the matrix material is provided preformed and added to the magnetic material. According to another embodiment, the polymer is preferably provided by polymerisation of a monomer in the presence of an unmagnetised magnetic material to form the magnetic particles comprising the magnetic material and a polymeric material. The monomer may comprise an organic monomer or an inorganic monomer, such as a silica-based monomer, depending on the desired polymer. Other inorganic monomers include organometallic monomers, sulfonitride monomers, phosphonitrilic monomers and monomers to form carborane coordination polymers. This polymerisation is not particularly limited but may comprise a step-growth condensation (also called a polyaddition reaction) and/or a radical reaction.

The polymerisation may take place in an emulsion in which the unmagnetised magnetic material is present in discontinuous phase thereof. According to this embodiment, the step of polymerisation preferably takes place in the discontinuous phase of the emulsion and the monomer is typically also present in the discontinuous phase of the emulsion, prior to polymerisation. The present invention is not limited to this system since it is also possible that some (or all) of the monomer may be in the continuous phase. After a chemical reaction takes place at the interface between the continuous and discontinuous phase it is made possible for the monomer to enter the emulsion droplets (discontinuous phase) prior to the polymerisation. The emulsion may be water-in-oil emulsion or an oil-in-water emulsion. Where the emulsion is a water-in-oil emulsion, the monomer generally comprises a water soluble organic and/or inorganic monomer. Where the emulsion is an oil-in-water emulsion, the monomer generally comprises a non-polar organic and/or inorganic monomer.

As an alternative to an emulsion-based system, the step of polymerisation may take place in solution followed by a coating of the magnetic material.

The magnetic material may comprise particles, the length or diameter of which is in the range 0.1 µm to 5000 µm, preferably 0.1 µm to 500 µm and most preferably 0.1 µm to 100 µm. A particularly preferred length or diameter for the magnetic material is in the range 100-300 nm.

In use, the magnetic particles according to the invention may be provided for separating a target substance from a sample containing such a target substance. The target substance may comprise a cell; a microorganism, which may be cellular or acellular; a metal such as a pure metal or compound comprising a minor or major part thereof; or an organic compound such as an environmental contaminant, a nucleic acid, or a protein.

One important target substance is a nucleic acid, which may be DNA, RNA, or a modified form thereof. Where the nucleic acid is DNA, this may be ds or ssDNA. Where the nucleic acid is RNA, this may be rRNA, mRNA or total RNA.

A nucleic acid-containing sample typically comprises a biological sample such as a cellular sample. The biological sample may or may not need to be pretreated, depending on its structure. For example, in the case of plant or fungal cells or solid animal tissue, pretreatment would be required as is known in the art. Samples stored in the form of a solid phase such as a paraffin section may also need pretreatment. Samples may be from foodstuffs, environmental samples or clinical samples and may contain prokaryotic or eukaryotic cells or other moieties such as mycoplasmas, protoplasts or viruses. Blood products are an important area for nucleic acid isolation and the present invention is particularly applicable to whole blood and other blood products such as plasma, serum and buffycoat.

Where nucleic acid is to be purified, the matrix material may comprise any material capable of binding nucleic acid, such as certain organic polymeric materials or silica-based materials. In one arrangement, the matrix material bears acid groups on its surface as described in GB0210766.2 filed on 10 May 2002 by the present applicant company. The acid groups preferably comprise an organic acid surface such as a carboxylic acid surface.

Among those acid groups useable according to this aspect of the present invention may be mentioned carboxy, sulpho and aryloxy groups. For example, the carboxy or sulpho groups may be linked to the solid phase by alkylene or arylene groups so as to form carboxylic or sulphonic acids. Aryloxy groups such as phenoxy groups may also be so linked and may incorporate further aromatic or aliphatic moieties. Carbon atoms in each type of organic acid may be substituted with heteroatoms. The presence of such heteroatoms and the optional presence of further functional groups on the surface, including esters, amines, alcohols, carboxylic acids, amides, halides, aldehydes, ketones, imines, nitro compounds, thiols, thioesters, nitriles, acid anhydrides and sulphonic compounds may each contribute to the properties of the solid phase, especially to the hydrophilicity of the solid phase. The preferred solid phase is hydrophilic because too hydrophobic a solid phase (for instance where there is too a high a concentration of polystyrene) will tend to give problems with nucleic acid binding.

Alternatively, the matrix material may comprise a silica-based material for binding nucleic acid. Silica-based magnetic particles may require the use of a chaotrope as part of the isolation process to promote binding of the nucleic acid to the particles.

The chaotrope generally comprises a chaotropic ion provided at a concentration sufficiently high to cause the nucleic acid to lose its secondary structure and, in the case of double-stranded nucleic acids, to melt. Chaotropes are thought to disrupt hydrogen-bonding in water so as to make denatured nucleic acid more stable than its undenatured counterpart. The chaotrope typically comprises a guanidinium salt, urea, or an iodide, chlorate, perchlorate or (iso)thiocyanate. Preferred chaotropes include guanidinium thiocyanate, and guanidinium hydrochloride.

The concentration of chaotrope typically present when contacted with the sample is in the range 2M to 8M.

In a further arrangement where the nucleic acid is the target substance, an affinant comprising an oligonucleotide may be used as a specific hybridisation probe for nucleic acid having a sequence complementary to the oligonucleotide sequence.

A step of separating the magnetic particles with the nucleic acid bound thereto from the liquid phase is generally required in order to remove contaminants in the liquid phase. Further washing steps may be applied to the solid phase at this point. Any conventional separation step for separating solid phase from liquid phase is applicable, including centrifugation and decanting of the liquid phase from the pelleted solid phase or using a column in which the solid phase is packed and the liquid phase passed through. Where the magnetic solid phase is used, this facilitates separation, which can be carried out in the presence of a magnetic field.

Depending on the form in which the isolated nucleic acid is required, a further elution step can be provided. In some cases it may be satisfactory for the nucleic acid to remain bound to the magnetic probe. This may be the case if further manipulations of the nucleic acid on a solid phase are required, such as an amplification step. Equally, the nucleic acid may be eluted from the solid phase by applying an elution solution, which may simply be water or a buffer.

According to further embodiments of the invention, the target substance may comprise a cell, protein, bacterium, virus, or environmental contaminant. The cells may be prokaryotic or eukaryotic cells. Eukaryotic cells include animal, plant and fungal cells. Prokaryotic cells include bacteria and blue green "algae". Other microorganisms include acellular microrganisms such as viruses and prions.

Suitable affinants may be selected which are known to bind each of these target substances. In one embodiment, the affinant is capable of binding a cell or a protein and preferably comprises an antibody, a binding protein, a fragment of an antibody or binding protein, or a ligand. The binding protein may comprise an avidin such as streptavidin or other biotin-binding affinant. According to this embodiment, the target substance is biotinylated. Alternatively, the avidin is bound to the target substance and the magnetic particles are biotinylated. In a further arrangement, the affinant comprises a ligand which comprises an oligonucleotide or a metal chelate specific for the target substance. The cell or protein may be microbial. The affinant may also be capable of binding a virus or a prion.

Where the target substance comprises cells, it is possible, for example, to introduce antibodies on the magnetic particles. The antibodies may be intact or present as an active fragment. Antibodies are typically introduced on the magnetic particles via covalent coupling of a ligand from the antibody to the surface of the magnetic particle, usually via the matrix material. Suitable ligands from the antibody include —OH, —$NH_2$ and —SH. Various coupling chemistries may be applied to couple the ligand of the antibody to the magnetic particle. For —OH it is possible for example to use epoxy, divinyl sulfone, or cyanuric chloride. For —SH, it is possible to use maleimide, iodoacetyl, pyridyl disulfide or epoxy activated matrices. For —$NH_2$ coupling it is possible to use epoxy, carboxylic acid/EDC, azlactones, aldehydes/$NaCNBH_3$, cyanogen bromide, N-hydroxy succinimides, carbonyl diimidazoles, organic sulfonyl chlorides and others.

It is also possible to tailor the chemistry of the matrix material so that it has affinity for the cell in question.

As a further option, introduction of one of avidin or biotin on the magnetic particles and introduction of the other onto the cells will enable the particles specifically to bind to the cells via an avidin-biotin binding interaction. Typically streptavidin is introduced to the magnetic particles. The cells may be biotinylated for instance by using biotinylated NHS or by allowing the cells to interact selectively with a reagent which comprises biotin coupled to a moiety which reacts specifically with the cells such as an antibody.

In the case where the target substance is a protein it is possible to introduce protein binding proteins which specifically target other proteins. One example is to introduce protein B on the magnetic particles to isolate humane IgA (Faulmann et at 1991. Equally, human IgA could be introduced on the magnetic particles to isolate protein B.

In another embodiment it is possible to isolate proteins using the specific chemistry of the magnetic particles. For example, oligonucleotides could be introduced on the magnetic particles as affinants for specific amino acids of the proteins. Alternatively, it is possible to use immobilised metal chelate affinity chromatography in which chelates are introduced onto the magnetic particles to isolate proteins via specific metal affinity domains of the proteins. One example of this is repeated Histidine tags on proteins which will have an affinity for immobilised nickel on the magnetic particles.

In a further embodiment, it is possible to use an avidin/biotin binding pair in the same way as for isolating cells.

Where the target substance comprises a microorganism such as a virus, bacterium or other microorganism, one strategy is to introduce antibodies or proteins on the magnetic particles which have an affinity for the proteins of the microorganism that are exposed on the cell membrane or surface. The methodology may be analogous to that used in isolating other cells. Alternatively, it is possible to introduce proteins that have affinity for the microorganism proteins in the same way as applied to isolating proteins as discussed above.

In a further embodiment, it is possible to use a hydrophobic surface to obtain depletion of the bacteria to that surface.

In a further embodiment, the target substance comprises a metal and the affinant comprises a chelator for the metal.

Where the target substance comprises a metal such as a pure metal or metal compound which may be necessary to be depleted from a sample for environmental reasons, it is possible to introduce a metal chelator on the magnetic particle. Examples include IDA or NTA for the specific binding of metal of choice. Chelation chemistry is well known to those skilled in this art and is discussed in the book by Hermanson et at (1992).

Instead of using an affinant to bind microorganisms, the matrix material may comprise a hydrophobic functional group capable of binding the microorganisms. Hydrophobic functional groups may also be used on the matrix material in order to bind hydrophobic target substances such as environmental contaminants. For example, PCBs have a hydrophobic structure which is capable of being bound by a hydrophobic surface on a matrix material. The hydrophobic surface may, for example, be obtained by using aromatic groups.

The magnetic particles according to the present invention may be used in a positive selection or a negative selection of the target substance. In a positive selection, the target substance is required for further use or further isolation and possibly purification. In positive selection it is preferred to avoid non-specific isolation of contaminating material. Easy disaggregation of the magnetic particles is extremely important in positive isolation to ensure good mixing and facilitate efficient washing of the particles with the target substance bound thereto. Isolation of nucleic acid is just one example of positive selection where the target substance is isolated from the sample.

In a negative selection, the target substance is depleted from the sample. The purpose of this is generally to clean the sample for future manipulation or use of the sample. Removal of contaminants such as environmental contaminants is one example of a negative selection. Another example of negative selection is where the target substance is T-cells and the sample is a blood sample.

The magnetic particles may be used in a cell sorting apparatus for positive selection or negative selection.

In a further aspect, the present invention provides a process for separating a target substance from a target substance containing sample, which comprises:

(a) providing target substance binding magnetic particles which comprise a magnetic material and a matrix material, wherein the magnetic material is remnant upon exposure to a magnetic field;

(b) providing a liquid phase comprising the target substance-containing sample;

(c) dispersing the sample with the magnetic particles so as to bind the target substance thereto; and (d) isolating the particles from the sample by applying a magnetic field thereto and separating the particles from the liquid phase.

The step of dispersing the sample with the magnetic particles preferably comprises subjecting the magnetic particles to disruption to disaggregate the particles. The disruption may comprise mechanical, acoustic or UV disruption. Mechanical disruption includes pipetting, stirring, vortexing and/or shaking so as to disaggregate the particles. Acoustic disruption includes ultra sonication and UV disruption. It is important that the sample is dispersed as fully as possible with the magnetic particles so as to maximise binding of the target substance thereto.

The process is useful for separating a target substance as defined above and may be used in a positive selection or a negative selection. Isolation of nucleic acid is a particularly important aspect of the invention, especially isolation of unfractionated nucleic acid such as total nucleic acid from a biological sample.

The process of the invention may include further steps. For example, where the isolated target substance is to be further purified or used in further manipulation, one or more washing steps may be incorporated into the process following binding of the target substance to the magnetic particles. In some cases the target substance may be used in a state bound to the magnetic particles. In other cases, there is a need to elute the target substance from the magnetic particles, for example, by applying an elution solution.

In a further aspect, the present invention provides a kit for separating a target substance from a sample containing such a target substance. The kit comprises magnetic particles as defined herein typically dispersed in a buffered aqueous solution and optionally including a component to inhibit microbial growth such as an azide. Sodium azide at 0.02% is a typical additive in such a buffered aqueous solution. The kit may typically further comprise one or more binding solutions, one or more washing solutions and one or more elution solutions each of which is generally aqueous. The elution solution may be aqueous or non-aqueous, depending on the target substance. Where samples require pretreatment, for example where biological samples incorporate material to be lysed, the kit will additionally include one or more lysis solutions.

Where nucleic acid is the target substance, the kit may appear in a standard format comprising a nucleic acid binding magnetic particle, together with one or more of the solutions discussed above. Where the nucleic acid binding magnetic particle is a silica magnetic particle, the kit may also include a chaotrope.

DETAILED DESCRIPTION OF THE INVENTION

The present invention is now described in more detail, by way of example only, with reference to the following Examples.

EXAMPLES

All Examples are performed in the absence of an applied magnetic field.

Example 1

In this example, an aqueous dispersion of ferrimagnetic magnetite particles in sodium silicate solution (water glass) is mixed with an oil phase to form a water-in-oil emulsion with magnetite in the aqueous phase. Condensation polymerisation is performed in the presence of acid to produce the magnetic particles with an inorganic polymer.

Ferrimagnetic magnetite particles (size 200-300 nm) 20 g were dispersed in 40 g waterglass (NMD) using an ultraturax mixing device. After mixing for 1 min at 16000 rpm, the speed was reduced to 13000 rpm and 300 ml of an oil phase (for instance toluene or isopar) containing 3% of an emulsifier (for instance span 80, span 65) was added. The speed was increased to 1700 rpm for 1 min and the resulting water in oil emulsion (magnetite dispersed in the water phase) was stirred in a reactor for 10 min at 20° C. before 2M $HNO_3$ (30 ml) was added. After stirring for 1 h and addition of methanol (30 ml), the suspension was stirred at 50° C. for 16 h. The magnetic particles were washed with methanol (3×150 ml), water (1×150 ml) and finally methanol (2×150 ml) using a centrifuge or a magnetic device. The particles were dried under vacuum. Particle size 0.3 µm-1.5 µm. Relative susceptibility: $35 \times 10^{-3}$ cgs.

Example 2

In this example ferrimagnetic magnetite particles are dispersed in an organic monomer (EGDMA) and an oil in water emulsion is formed by mixing the particle suspension with an aqueous phase. The monomers are polymerised to produce the organic polymer magnetic particles.

Ferrimagnetic magnetite particles (size 200-300 nm) 6.6 g were dispersed in 20 g EGDMA. AIBN (0.45 g) was added to the dispersion and the organic phase containing magnetite was emulsified in water (150 ml) containing 0,5% polyvinylalcohol (Evanol) by use of an ultraturax (13000 rpm, 2 min). The resulting emulsion was stirred in an reactor for 20 h at 65° C. and the magnetic polymer beads were washed with methanol (5×150 ml) and dried at 80° C. for 6 h. Particle size 0.7 µm-6 µm. Relative susceptibility: $15 \times 10^{-3}$ cgs.

Example 3

In this Example ferrimagnetic magnetic particles are dispersed in an organic solvent with a monomer, which is then polymerised to form the particles.

Magnetite (1 g) is dispersed in an organic solvent such as THF, hexane or toluene (10 ml), where after an epoxiresin like bisphenol-A (10 ml) is added. Stirring is continued at 70° C. for 16 h and the magnetic particle are then washed 5 times with THF (25 ml each wash) by using a centrifuge. Finally the particles are dried in vacuum at 50° C. The particles have approximately 0.25 mmol/g epoxigroups.

Example 4

In this Example ferrimagnetic magnetic particles are dispersed in an organic solvent with a prepolymerised polymer to form the particles.

Dry ferrimagnetic magnetite particles (size 200-300 nm) 1 g were dispersed in 10 ml of 0.5% poly(ethylene) imine (Aldrich, Mw 35 000) in 0.1 M Na-carbonate pH 9.5. The suspension was allowed to incubate at ambient temperature for 3 h, where after the particles were washed with 4×20 ml water.

Introduced polymers were confirmed by surface charge measurements (Malvern Zetaziser). The surface of the magnetic particle had a positive shift in isoelectric point of 1 magnitude.

The invention claimed is:

1. A process for separating a target substance from a sample containing the target substance, the process comprising:
   (a) providing magnetic beads in a liquid, wherein each magnetic bead includes a magnetic material coated with a matrix material, the matrix material having an affinity for the target substance and having a surface comprising hydrophilic functional groups which promote disaggregation of the magnetic beads in the liquid, the magnetic material including one or more magnetic particles comprising ferrimagnetic, metal oxide and having a length or diameter of about 100 nm to 300 nm, and wherein the magnetic beads form aggregates due to remanent magnetization in the absence of a magnetic field;
   (b) disrupting the aggregates by an external force to form a dispersion of the magnetic beads suspended in the liquid;
   (c) contacting the dispersion of the magnetic beads with the sample containing the target substance to allow the target substance to bind to the magnetic beads; and
   (d) extracting the magnetic beads bound to the target substance from the sample by applying a magnetic field to thereby separate the target substance from the sample.

2. The process according to claim 1, wherein disrupting the aggregates comprises mechanical disruption selected from pipetting, stirring, vortexing, shaking, sonication and UV disruption.

3. The process according to claim 1, wherein the target substance is a cell, a microorganism, a protein, a metal, an organic compound, or a nucleic acid.

4. The process according to claim 1, wherein the sample comprises unfractionated nucleic acid.

5. The process according to claim 1, wherein the target substance is a contaminant which is depleted from the sample.

6. The process according to claim 1, wherein the ferrimagnetic metal oxide comprises ferrimagnetic magnetite.

7. The process according to claim 1, wherein the liquid is an aqueous liquid.

8. The process according to claim 1, wherein the matrix material comprises an affinant for binding the target substance.

9. The process according to claim 8, wherein the affinant is capable of binding a cell, a protein, a vims or a prion.

10. The process according to claim 9, wherein the cell or protein is microbial.

11. The process according to claim 8, wherein the affinant comprises an antibody, a binding protein, a fragment of an antibody or binding protein, or a ligand.

12. The process according to claim 11, wherein the affinant comprises a binding protein which comprises an avidin for binding to a target substance which, is biotinylated, or the affinant comprises biotin and the target substance is avidinylated.

13. The process according to claim 11, wherein the affinant comprises a ligand which comprises an oligonucleotide or a metal chelate specific for the target substance.

14. The process according to claim 8, wherein the target substance comprises a metal and the affinant comprises a chelator for the metal.

15. The process according to claim 1, wherein the matrix material is an organic polymer or a silica-based polymer.

16. The process according to claim 1, wherein the matrix material is an organic polymer, the magnetic particles are 200-300 nm in length or diameter, and the magnetic beads are 0.7-6 μm in sizes.

* * * * *